United States Patent [19]

McDonald et al.

[11] Patent Number: 4,987,886
[45] Date of Patent: Jan. 29, 1991

[54] TRACTION APPARATUS

[76] Inventors: Philip McDonald, 3326 Elgin Dr.; Newel Kimball, 204 Browning Ave. #5, both of, Salt Lake City, Utah 84109

[21] Appl. No.: 433,751

[22] Filed: Nov. 9, 1989

[51] Int. Cl.$^5$ .......................... A61H 1/02; A61F 5/08; A61F 5/04
[52] U.S. Cl. .................................. 128/75; 128/76 R; 128/84 C
[58] Field of Search ............... 128/75, 76 R, 78, 84 R, 128/84 C, 87 A, 87 B, 97, 87 R, 878, 69, 71

[56] References Cited

U.S. PATENT DOCUMENTS

| | | | |
|---|---|---|---|
| 2,673,694 | 3/1954 | Howell | 128/84 C |
| 2,997,250 | 8/1961 | Collins | 128/84 R |
| 3,336,922 | 8/1967 | Taylor | 128/75 |
| 3,359,976 | 12/1967 | Laval, Jr. | 128/75 |
| 3,795,243 | 3/1974 | Miller | 128/75 |
| 3,871,366 | 3/1975 | Cotrel | 128/75 |
| 3,888,243 | 6/1975 | Powlan | 128/75 |
| 4,015,597 | 4/1977 | Beaver | 128/75 |
| 4,161,946 | 7/1979 | Zuesse | 128/75 |
| 4,220,147 | 9/1980 | Allen, III | 128/75 |
| 4,508,109 | 4/1985 | Saunders | 128/75 |
| 4,632,099 | 12/1986 | Mollo | 128/75 |
| 4,732,144 | 3/1988 | Cunanan | 128/75 |
| 4,790,301 | 12/1988 | Silfverskiold | 128/87 A |
| 4,793,334 | 12/1988 | McGuinness et al. | 128/87B |

OTHER PUBLICATIONS

G. J. Wang, J. T. Moskal, T. Albert, C. Pritts, G. M. Schuch and W. G. Stamp, *The Journal of Bone and Joint Surgery,* "The Effect of Halo-Vest Length on Stability of the Cervical Spine", 1988.
Instructions for Operating the Exo-Bed Traction Unit.
The Lossing Orthopedic Company, "Necktrac ®, Instructions for Treating Patients," 1982.
Med-Trak, Inc., "Clinical Application and General Considerations in the Use of Home Cervical Traction," pp. 1–8.
Dr. John P. Boren, MedTrak Research Labs, Inc., "Conservative, Safe and Effective Treatment of Pain."
Shamrock Medical, Inc., "Econo-Cerv Home Care Supine Cervical Traction".
Hill Laboratories Co., "Hill Cervical Traction Device."
Medipedic, "Rigid Cervical Collars."
Medipedic, "Goodley Polyaxial Cervical Traction."
Medipedic, "Bed Cervical Traction" and "Door Cervical Traction."
Medipedic, "Head Halters."
Granberg International, "E3000 EZ Tract Information Packet."
The Sukoff Traction Device, Specifications.
Shamrock Medical, Inc., "C-Flex Supine Cervical Traction."
Physical Therapy, vol. 66, No. 8, Aug. 1986, "Goodley Polyaxial Cervical Traction, A New Approach to a Traditional Treatment," by Grace L. Walker, pp. 1255-1259.

Primary Examiner—Robert A. Hafer
Assistant Examiner—Michael Brown
Attorney, Agent, or Firm—Thorpe, North & Western

[57] ABSTRACT

Traction apparatus for applying a traction force to a person's neck and spine including a frame assembly, a spring assembly and attachment assemblies. A first frame embodiment allows the patient to be ambulatory while traction is being pulled on the neck and spine. A second embodiment of the frame is used when the patient is in a lying position. Both frames are designed such that the traction force passes from a point of attachment of upper and lower portions of the frame assembly, which is located at the base of the user's neck through an apex of the frame assembly where the spring assembly is located. Also included are specifics to two embodiments of the spring assembly. The first embodiment being a constant force spring. The second embodiment including a torsion spring in which the traction force can be adjusted. The spring assembly is attached to the frame assembly at the apex thereof and the frame assembly is secured either directly to the body of the user as in the ambulatory embodiment thereof, or is held in position under the user's body by the user's own weight while lying thereon. The spring assembly is attachable to most common types of headgear to cause traction to be pulled on the head and neck of the user.

10 Claims, 8 Drawing Sheets

TRACTION APPARATUS

BACKGROUND OF THE INVENTION

The invention relates generally to traction apparatus, and more specifically to a portable traction frame and spring assembly for applying traction forces on a person's neck and spine.

Traction devices for applying a prolonged pulling or traction force on the spine to correct dislocations, relieve pressure and for other therapeutic purposes have been in general use for a long time. It is common for such traction devices to apply a longitudinal force to a person's head directed away from his body resulting in a traction force on his neck and spine. A background of traction devices in general is presented in applicant's co-pending U.S. Patent Application, Ser. No. 07/435272, filed 11/09/89 and incorporated herein by reference.

In the prior art, there have been a substantial number of traction frames or other devices for applying cervical traction to the head of the user. One category of these traction frame devices, such as shown in U.S. Pat. No. 4,220,147, employs an anchor device in the form of an A-frame detachably connectable to the back of a spine board on which a person may be laid. The A-frame includes an adjustable mechanism for applying tension to a traction sling which is attached to the person's head. However, these types of devices have several drawbacks. For example, the traction force pulled on the user's head causes a large rotational moment of force to be placed on the frame caused by the orientation of the frame members relative to the direction of the traction force pulling thereagainst. Also, these types of frames require a specially modified bed or traction board in order to be properly assembled for use.

Further, because of the large moment applied to the frame by the traction force, the frame must be either reinforced or built of heavy or high strength materials which cause the frame to be heavy, expensive, difficult to fold flat or otherwise make portable.

Finally, these types of traction devices do not allow for ambulatory use by the patient.

SUMMARY OF THE INVENTION

It is an object of the present invention to provide a traction apparatus for providing traction to the cervical spine which allows for traction forces to be applied substantially along or parallel to the plane of the frame assembly to minimize or eliminate moment loading thereof.

Another object of the present invention is to provide a traction apparatus which can be used on patients lying in a supine position or on patients which are ambulatory.

It is further an object of the present invention to provide a traction apparatus for ambulatory use which can provide a controlled angle of traction force to the user's head whether in the sitting or standing position.

A further object of the present invention is to provide a traction apparatus for use on ambulatory patients which also promotes correct posture by isolating the trapezius muscles, encouraging elongation of the neck, and allowing for posture improving exercises to be performed by the patient during treatments.

It is further an object of the present invention to provide a traction apparatus for use on patients which is compact and can be folded into a substantially flat configuration, and which requires no attachment to outside apparatus such as a bed, wall, table or the like for its stabilization.

A further object of the present invention is to provide a traction apparatus for patients in the supine position which is held in a stable position by the patient's own body while in use.

A further object of the present invention is to provide a traction apparatus having a spring assembly which can be easily removed and replaced with a different spring assembly.

A further object of the present invention is to provide a traction apparatus including a torsion spring assembly which allows for adjustment of the traction force applied to the user's head.

A further object of the present invention is to provide a traction apparatus which includes a constant force spring assembly which allows the application of the proper traction force without the necessity of adjustment of the spring assembly.

A further object of the present invention is to provide a traction apparatus which is portable, compact, and lightweight in design, and which is simple in operation to allow it to be useful, not only in a hospital setting but also for emergency and/or home use.

The above and other objects of the present invention are realized in a traction apparatus which includes a frame assembly, an attachment assembly and a spring assembly. One embodiment of the frame assembly includes a base portion having hook shaped attachment members for attachment to the shoulders and torso (and waist, if desired) of the patient, and which may include pads, straps, belts or other like devices for securing the base portion of the frame assembly to the user's upper body. The frame further includes an A-shaped upper portion which has a spring assembly location at the apex thereof and which is attached to the base portion by a pair of attachment assemblies. The attachment assemblies being in the form of hinges which are located above each of the shoulders at the base of the neck of the user. The hinges allow the A-shaped portion of the frame to be adjusted to extend above the user's head at any angle desired. The angle to which the upper portion of the frame is adjusted is determined so as to limit the moment loading thereon caused by traction forces generated by the spring assembly when in use. The upper portion of the frame can be completely planar in design or may have a small arched portion adjacent the apex thereof for facilitating the user's access to the spring assembly for purposes of attachment and adjustment of the spring assembly to the user's headgear.

A second embodiment of the frame assembly includes a base portion which has a base frame and back pad upon which the user lies. The frame assembly further includes an upper portion which extends above the user's head when lying on the base portion and which is also of an A-frame shape and which also has a location at its apex for accepting a spring assembly. The base portion and upper portion of the frame assembly are also attached by an attachment assembly which again takes the form of a pair of hinges located next to the user's shoulders at the base of the user's neck when the user is lying on the base portion. This hinge connection between the base portion and the A-frame portion allowing the A-frame to be adjusted above the user's head at the desired location to allow for low moment loading of the A-frame portion by the traction forces applied by the spring assembly to the user's head.

The spring assembly of the traction apparatus of the present invention can also include several embodiments. A first embodiment being a constant force spring which comprises a spool about which a spring such as a thin, flat steel band, or a plurality of thin, flat steel bands leafed together, are attached to a spool which is rotatably attached at the apex of the A-shaped portion of the frame assembly. The bands being attached to the spool at one end thereof and having a hook member attached at the opposite end thereof. A handle attached at the hook member allows it to be pulled away from the spool, causing the spool to rotate at its attachment location to the frame, and be attached to the user's headgear in order to apply traction force to the user's head.

A second embodiment of the spring assembly includes a torsion spring which is located inside a bifurcated spool, one portion of the spool being attached to a strap which is attachable to the headgear for pulling a traction force on the user's head, and the second portion of the spool being attached to an adjustment bar which can be rotated by the user to adjust the tension force applied to the user's head. The traction force is supplied by a spring which is located on the interior of the spool, each end of the spring being attached to opposite portions of the spool so that relative rotation of one side of the spool with the other side causes a winding or unwinding of the spring to allow generation of the traction force desired.

Other types of traction force generating devices may be used in conjunction with the present invention in lieu of the above-identified spring assemblies. For example, it is within the scope of the present invention to employ a motorized or hydraulically driven traction force generating device so long as the device used can be at least partially mounted at the apex of the frame assembly and can be made to generate traction forces in a direction substantially parallel to the plane of the A-frame, or in the case of a frame assembly having an arched apex, to generate traction forces which lie substantially along an imaginary plane defined by the apex of the frame and the attachment assemblies.

Further, modifications directed to the above-noted torsion spring which include a single or dual clutch for limiting the amount of traction force generatable by the torsion spring, and for locking the spring in predefined torqued positions corresponding to predetermined traction forces is contemplated and will be the subject of a copending U. S. Patent Application of the present inventors.

BRIEF DESCRIPTION OF THE DRAWINGS

The above and other objects, features and advantages of the invention will become apparent from a consideration of the following detailed description presented in conjunction with the accompanying drawings wherein like features are identified with like numerals, in which.

DETAILED DESCRIPTION OF THE INVENTION

Figure 1:
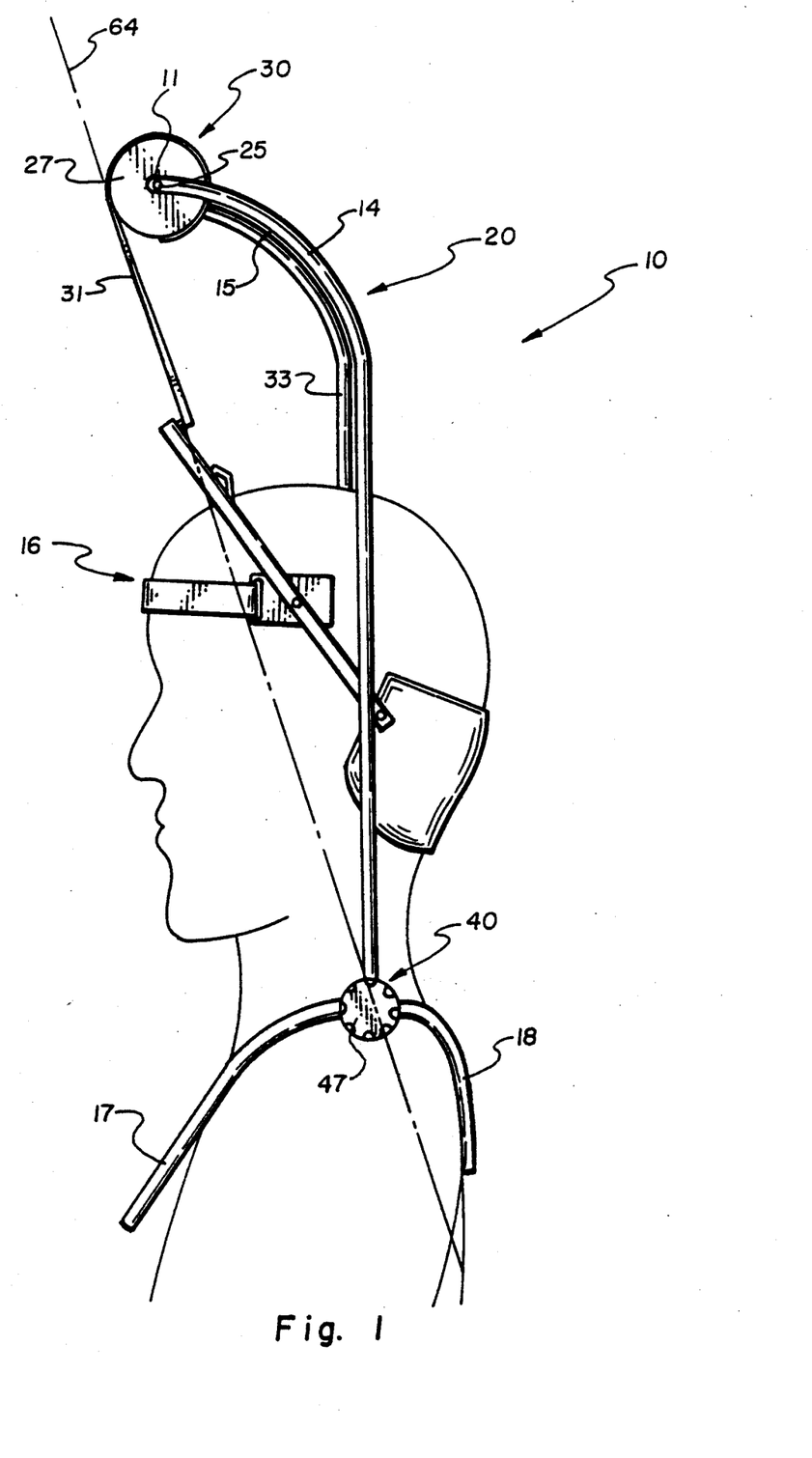
FIG. 1 is a side elevational view of one preferred embodiment of the traction apparatus of the present invention attached to a user in a sitting or standing position.

The traction apparatus 10 of the present invention as seen in FIG. 1 properly positioned on a user, is shown to comprise a frame assembly 20, a spring assembly 30, and attachment assembly 40. The spring assembly 30 being attached to the apex 11 of the frame assembly 20 at a position where it will be located above the head of the user when in place therein.

Figure 2:
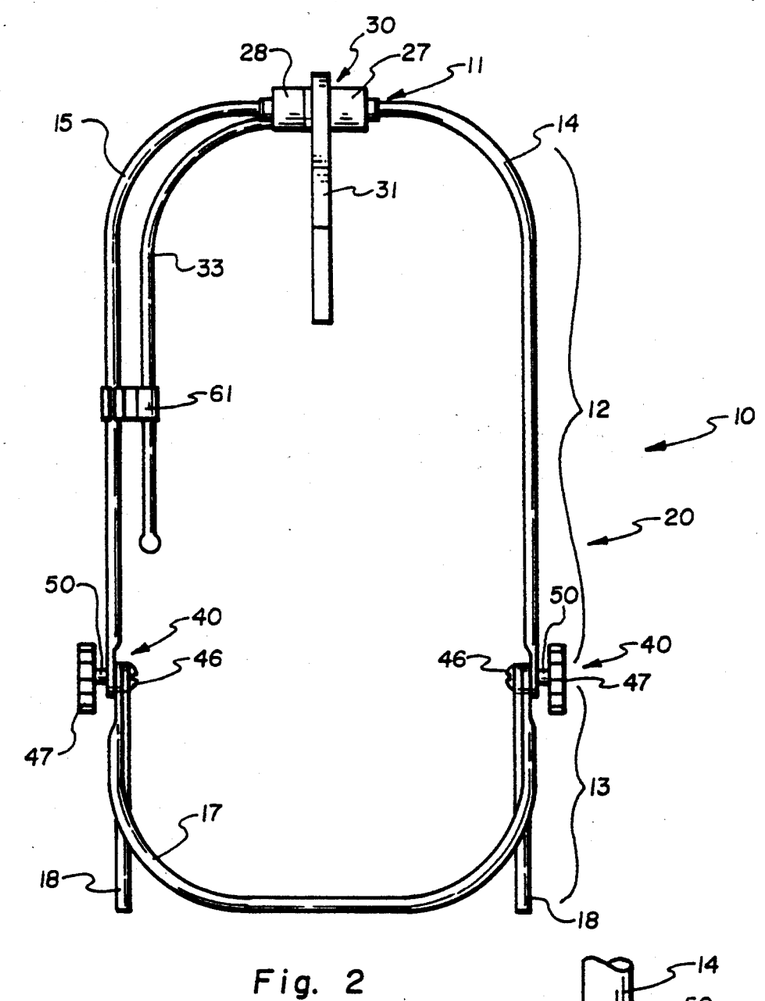
FIG. 2 is a front perspective view of the traction apparatus of FIG. 1.

As best seen in FIG. 2, the frame assembly 20 is comprised of two essential parts. An upper A-frame portion 12 which extends from the user's shoulders to a location above the head to which a traction force generating assembly such as the spring assembly 30 is attached, and a lower portion 13 which is attachable to the user's body about the shoulders and torso.

Figure 4:
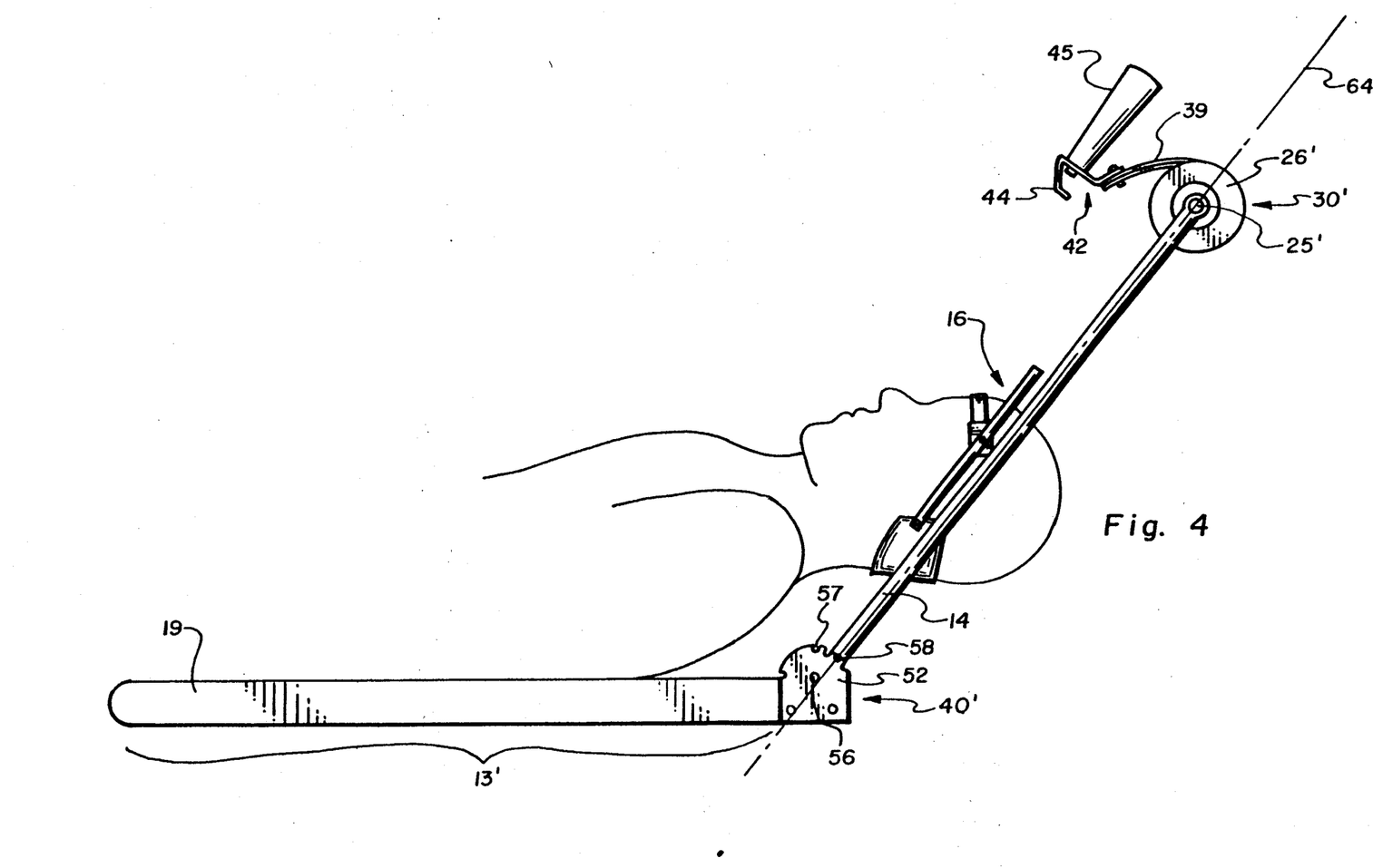
FIG. 4 is a side elevation view of another embodiment of a traction apparatus of the present invention on a patient who is lying in a supine position.

In a second embodiment of the invention as shown in FIG. 4, the lower portion 13 of the frame assembly 20 is fixed in a position relative to the body by the weight of the user's body itself being located thereon.

As best seen in FIG. 2, the upper portion of the frame assembly includes first and second elongate brace members (14 and 15, respectively) which extend from their attachment at the attachment assembly 40 to an apex 11 where the end of each brace member is attached to opposite sides of a spring assembly 30 in a manner as will be explained momentarily. The first and second brace members 14 and 15 may be completely linear along their entire length, as shown in FIG. 4, or may be arched at their ends adjacent the spring assembly 30 in order to cause the spring assembly 30 itself to be located slightly forward of the remainder of the A-frame 12 in order to facilitate the user's attachment between the spring assembly 30 and the headgear 16, and to facilitate the adjustment of tension forces generated by the spring assembly 30.

The brace members 14 and 15 may be longitudinally adjustable as by forming them of several telescoping members (not shown) or by the inclusion therein of a hydraulically actuated piston (also not shown) which may extend or shorten the length thereof in an adjustable manner. Such modifications to the basic embodiments of the present invention are anticipated and can be useful as a secondary means for adjusting the location of the spring assembly 30 or 30' above the user's head and as a secondary means for adjusting the tension applied by the torsion spring assembly 30.

The lower or base portion 13 of the frame assembly 20 as shown in FIG. 1, includes a front shoulder harness 17 and a pair of rear shoulder harnesses 18 which may be formed as an integral unit or may be formed as separate members as shown and attached together and to the A-frame 12 at the attachment assembly 40. The attachment assembly 40 can allow the front and rear shoulder harnesses to be adjusted to fit snugly over the user's shoulders and torso area in a manner as will be later explained.

Although not necessary, the rear shoulder harnesses 18 may extend a sufficient length so as to reach to the lower back of the user, if desired, and be attached to a waist belt or the like in order to be more securely supported. The attachment of the harnesses 18 to a waist belt may be either in the form of a rigid or gimbaled attachment.

Likewise, the front shoulder harness 17 may be secured around the chest or upper torso of the user as by means of straps or the like. Further, the entire set of shoulder harnesses may be padded at any desired location to ensure the comfort of the user while in use.

Figure 5:
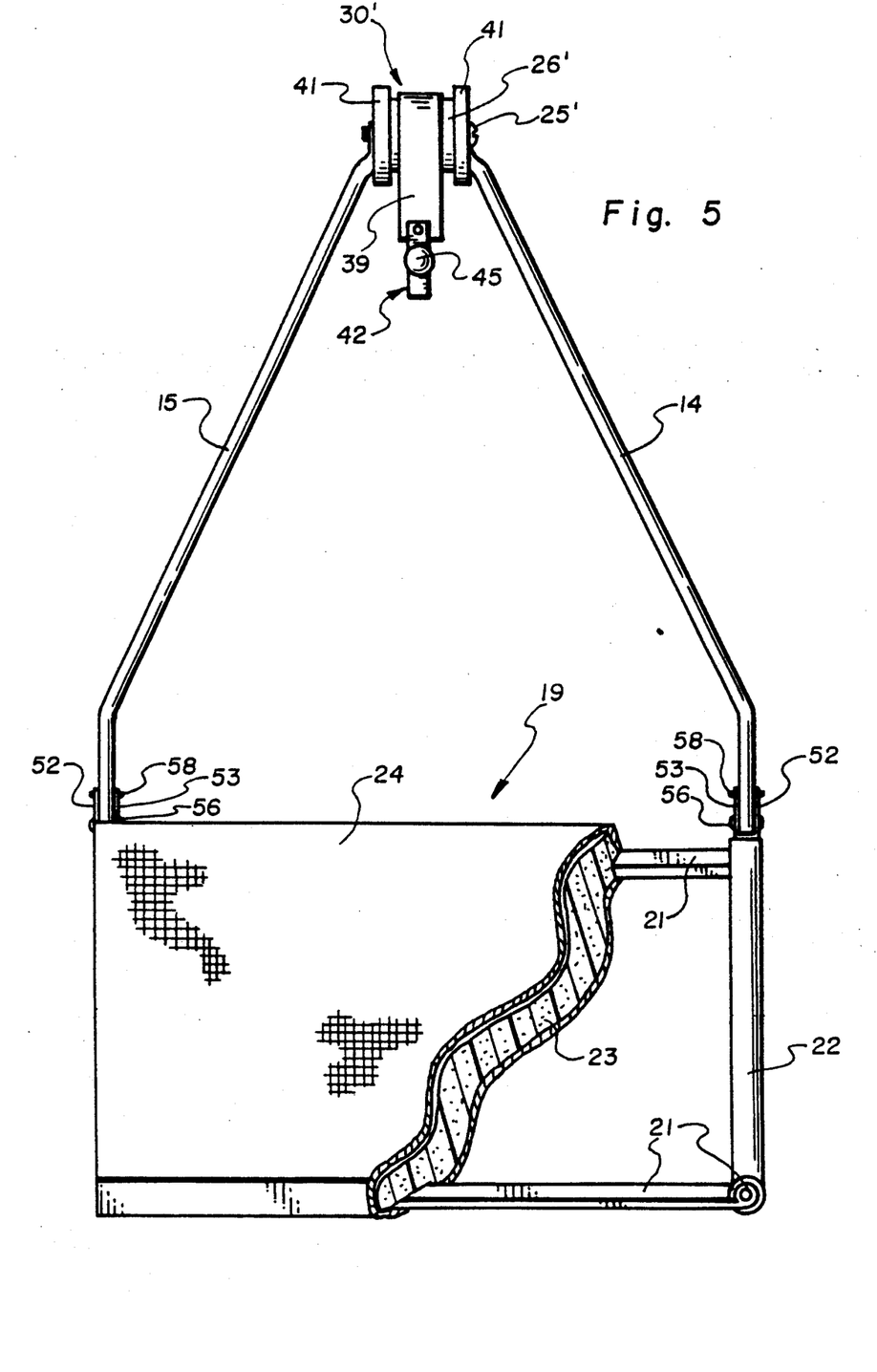
FIG. 5 is a front elevation view of the traction apparatus of FIG. 4.

The base portion 13' of the frame assembly 20 as shown in FIG. 5, includes a rectangularly shaped base member 19 having a rectangularly shaped frame 21 which may be padded with pad 22 for the comfort of the user. The interior of the frame may also be filled with a padding material 23, and the entire base member 19 may be enclosed in an envelope 24 of fabric or other soft pliable material. The base member 19 needs to be of a sufficient size to allow the user to place at least a substantial portion of his torso area thereupon when using the device. For example, the base member 19 may be placed upon a flat surface such as a floor, bed or table and the user lies with his back placed thereagainst as best seen in FIG. 4, in such a manner that each of the attachment assemblies 40' are located adjacent his shoulders at the base of each side of his neck. The weight of the user on the base member 19 is sufficient to stabilize the traction apparatus 10 and to hold it in its proper position during use.

As best seen in FIG. 2, the spring assembly 30 is attachable to the apex of the frame assembly 20 by means of a bolt 25 or the like and is rotatable relative thereto. Likewise, spring assembly 30' in FIG. 5 is attached to the frame assembly 20 in a similar manner.

Figure 8:
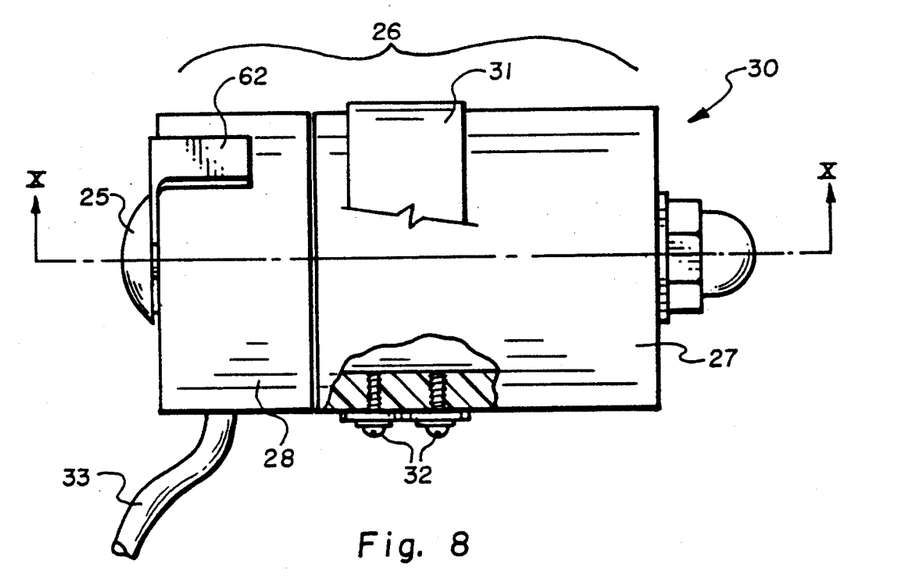
FIG. 8 is a front view of one embodiment of the spring assembly of the traction apparatus of the present invention.
Figure 9:
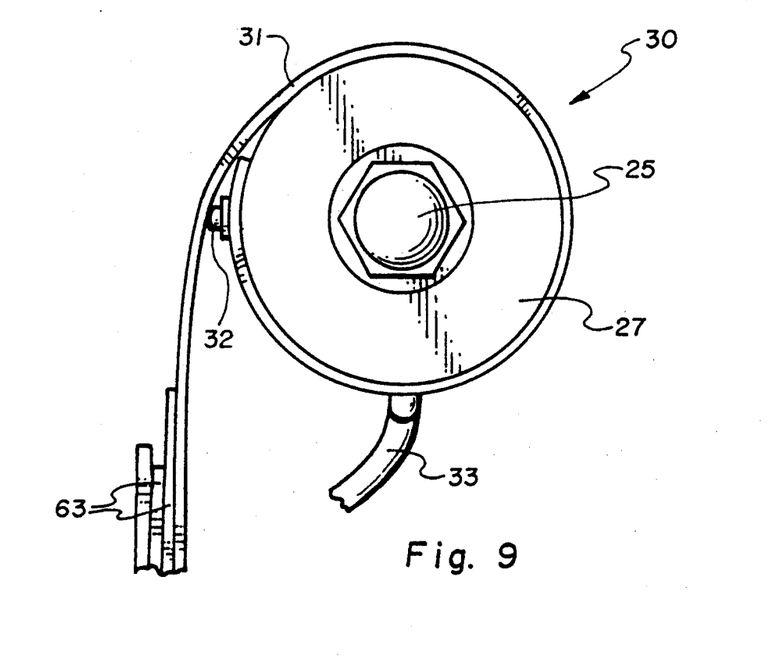
FIG. 9 is a side view of the spring assembly of FIG. 7.
Figure 10:
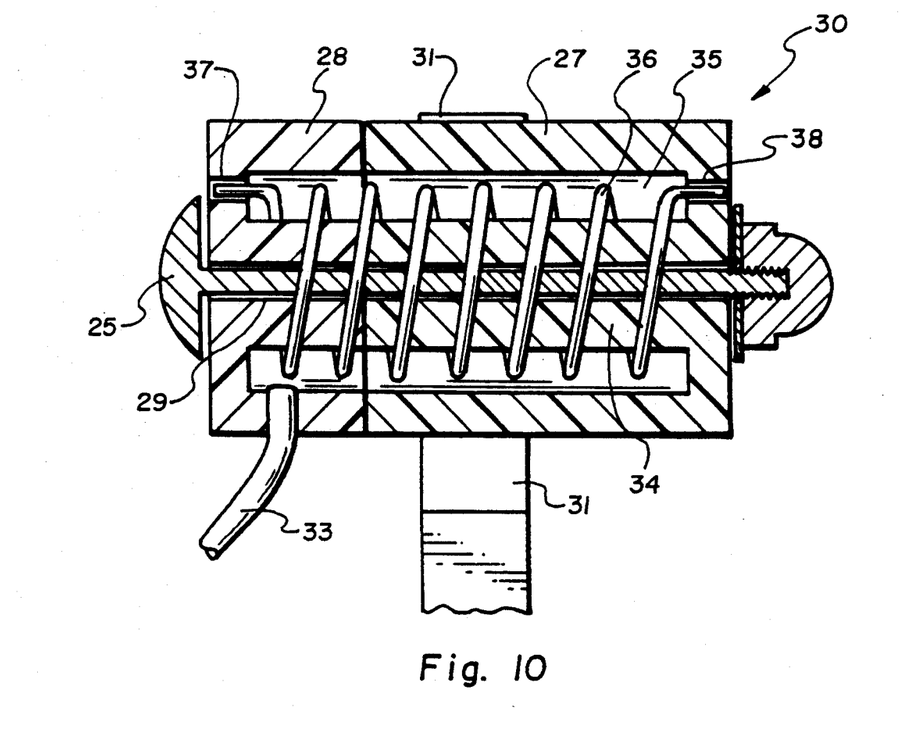
FIG. 10 is a cross-sectional view of the spring assembly of a traction apparatus taken along lines X—X of FIG. 9.
Figure 11:
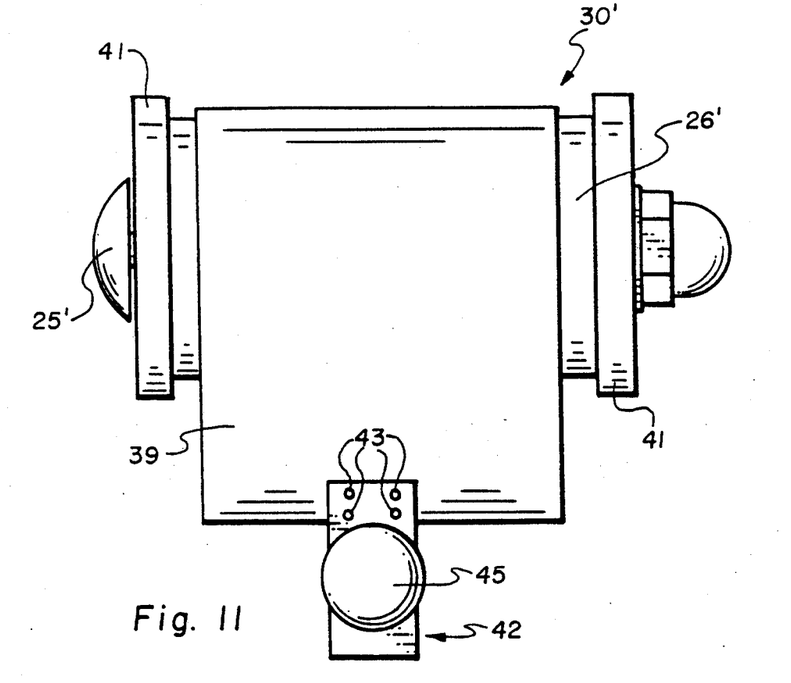
FIG. 11 is a front view of another embodiment of a spring assembly of a traction apparatus of the present invention.
Figure 12:
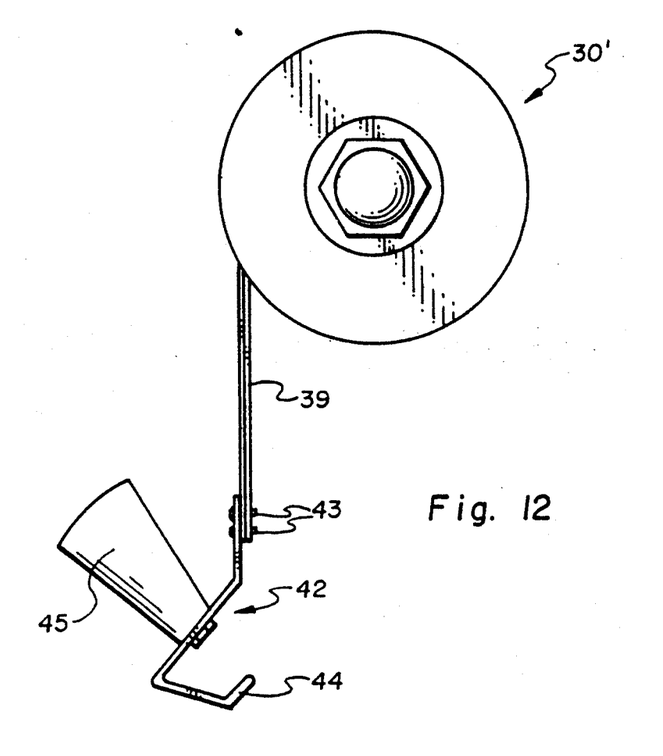
FIG. 12 is a side view of the spring apparatus of FIG. 11.
Figure 13:
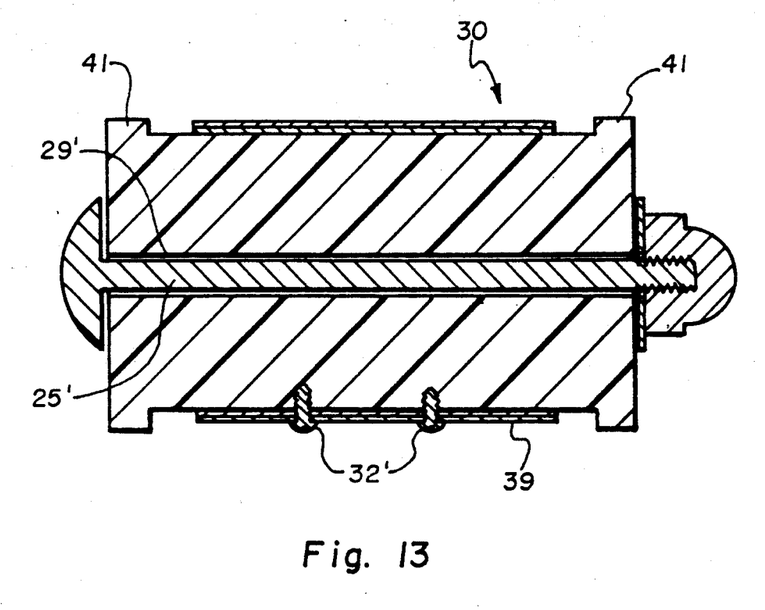
FIG. 13 is a cross-sectional view taken along lines XIII—XIII of FIG. 11.

FIGS. 8-10 show the torsion spring embodiment of the spring assembly (the spring assembly identified as 30), and FIGS. 11-13 show the constant force spring embodiment of the spring assembly (the spring assembly identified as 30'). In reference to FIGS. 8-10, the torsion spring assembly 30 comprises a spool 26 having a first hollow bifurcated portion 27 and a second hollow bifurcated portion 28. The exterior of the spool 26 is generally cylindrical in shape having an opening 29 through the longitudinal axis thereof for placement of the attachment bolt 25 therethrough which attaches the spool 26 to the frame assembly 20.

The first bifurcated portion 27 of the spool has attached to its outer surface a strap 31 having hook and loop attachment fabric 63 secured thereon, by means of screws 32 or the like, which can be extended from a rolled up position around the spool 26, to an extended position to attach to a headgear 16 useful for cervical traction, such as the headgear 16 shown in FIG. 1.

Although any common headgear useful for cervical traction may be used with the present invention, the headgear shown in FIG. 1 is specifically adapted for use with the present invention and is more specifically described in applicant's co-pending U.S. Patent Applicant Ser. No. 435272 filed 11/09/89, incorporated herein by reference.

The exterior surface of the second bifurcated portion 28 of the spool 26 includes an adjustment arm 33 which facilitates rotation of the second portion 28 with respect to the first portion 27 of the spool 26. Relative rotation of the two portions of the spool 26 effectively increases or decreases the tension force applied to the headgear 16 in the manner which will be explained below. The adjustment arm limitation bar 62 can be attached to bolt 25 and extend above the surface of the second bifurcated portion 28 of the spool. The limitation bar is locked to the bolt 25 and prevented from rotating when the adjustment bar 33 meets limitation bar 62, it cannot further rotate in that direction. The limitation bar 62 therefore keeps the adjustment bar within convenient reach of the user when in the process of attaching the apparatus to himself and adjusting the spring tension.

As best seen in FIG. 10, the interior of the spool 26 includes an interior cylindrical portion 34 which defines the bolt channel 29 and which also defines a cavity 35 in which a torsion spring 36 is located. The torsion spring 36 being attached to the spool 26 by one of its ends being inserted into an opening 37 in one end of the spool, and its other end being inserted into opening 38 at the opposite end of the spool 26. As can be readily seen, with the torsion spring 36 attached to the two opposite ends of the spool 26, rotation of one bifurcated portion of the spool relative to the other bifurcated portion is resisted by the spring 26. Traction force can then be generated and adjusted by either a winding or an unwinding of the torsion spring as by means of the above-mentioned adjustment bar 33, or by any other means functioning to increase the lever arm length in order to avoid difficulty in causing the relative rotation.

A constant force spring assembly 30', best seen in FIGS. 11-13, is also attachable to the apex 11 of the frame assembly 20 by means of a bolt 25' or the like and is rotatable relative thereto. The constant force spring assembly 30' comprises a solid spool 26' of generally cylindrical shape having an axial opening 29' therethrough for receiving the bolt 25' which attaches it to the apex 11 of the frame assembly 20. The exterior surface of the spool 26' has attached thereto a constant force spring 39. The spring 39 may be formed of a single band of metal or plastic which is coiled about the spool 26 and held in place in the center of the cylindrical outer surface by means of ridge members 41 formed adjacent each end of the cylindrical exterior surface. The spring 39 is attached to the spool 26' by means of screws 32' or the like at one end thereof, and the opposite end thereof is attached to a hook member 42. The hook member 42 may be attached to the band such as by rivets 43 or the like and must extend beyond the end of the spring 39 a sufficient distance to allow the hooking portion 44 thereof to be easily attachable to a headgear 16.

The hook member 42 may also comprise a handle 45 rigidly attached thereto which preferably extends in a direction perpendicular to the direction which the spring 39 must be pulled from the spool 26' when being attached to the headgear 16. The handle 45 can be grasped by the user and pulled straight away from the spool 26' a short distance until the hooking portion 44 of the hook member 42 can be attached at the proper location on the headgear 16.

The constant force spring 39 may include a plurality of bands of metal or plastic, if desired. Each band would lie in direct contact with the next adjacent band in a layered or leafed formation. Further, each band may be formed of the same materials and have the same dimensions as adjacent bands, or each may be different as desired in order to achieve a predetermined amount of constant traction force which will be generated thereby.

The spring 39 and spool 26' may be covered by a fabric or plastic cover (not shown) which can include an elongate tubular portion which matches the exterior surface of the spring 39, and a cylindrical portion attached to one end of the elongate portion which can be mounted around the spool. Preferably the cylindrical portion comprises a pair of wide straps having attachment devices, such as loop and hook material, which allows the band to be inserted through the elongate portion until the straps can extend around the spool 26' and attach to each other. The fabric cover can also be securely attached at the end of the spring 39 adjacent the hook member 42. In this manner, the cover can not only function as a covering for the spring 39, but also to limit the distance at which the hook member 42 can be pulled away from the spool 26', thus preventing overextension of the spring 39.

Figure 3:
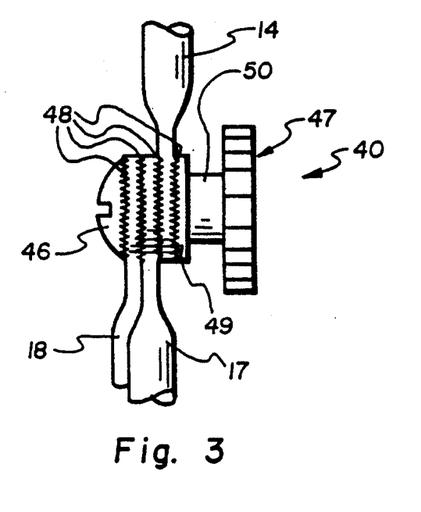
FIG. 3 is an enlarged view of the hinge of the apparatus of FIG. 1.

As best seen in FIG. 3, one preferred embodiment of the attachment assembly 40 includes a bolt 46 which passes through the brace member 14 (or 15) and the shoulder harnesses 17 and 18, to be threadably attached to an adjustment knob 47. The brace member 14 and shoulder harnesses 17 and 18, at the connection thereof with the attachment assembly 40 being stamped or otherwise formed into a set of radially extending teeth or corrugations 48 which allow them to mesh with each other and prevent relative movement when the knob 47 is securely tightened. A washer 49 may be placed between the cylindrical extension 50 of the knob 47 and the adjacent corrugated surface in order to allow the knob to be more easily rotated.

When the knob 47 is securely tightened, the corrugations 48 of each of the brace and harness members are forced into interlocking orientation to prevent any relative movement therebetween when the apparatus is in use. When it is desired to reorient any of the brace 14 or 15 or harness members 17 and 18 relative to any other, the knob 47 is loosened as sufficient distance to allow the corrugations 48 of the particular member to be moved out of interlocking relationship with the other members. The member is then rotated to the desired location and the knob 47 is retightened.

Figure 6:
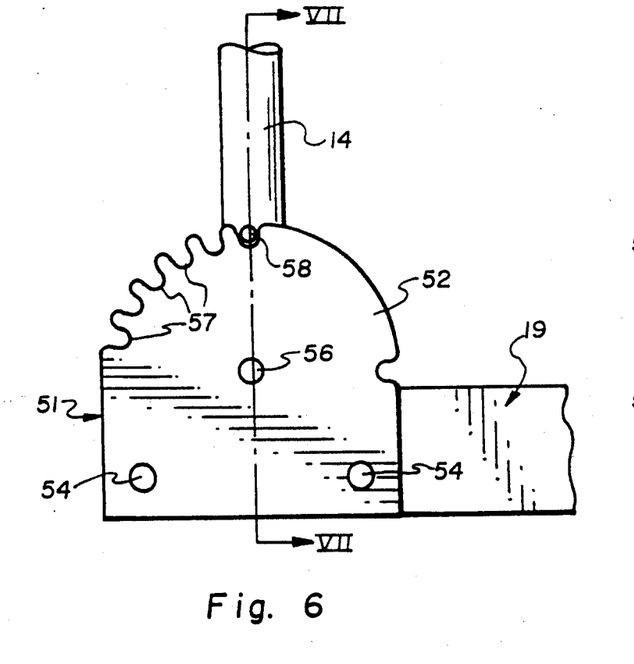
FIG. 6 is an enlarged view of an attachment assembly of the apparatus as shown in FIG. 4 made in accordance with the principles of the present invention.
Figure 7:
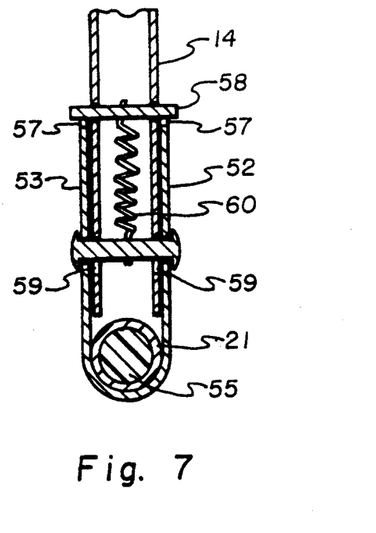
FIG. 7 is a partial cross-sectional view of the attachment assembly of FIG. 6 taken along line VII—VII thereof.

FIGS. 6 and 7 show another embodiment of the attachment assembly 40' of the present invention. In this embodiment, an elongate plate 51 having semi-circularly shaped ends 52 and 53 is bent to form a U-shaped channel into which a brace element 21 of the base member 19 as by means of rivets 54 or by means of welds, screws or the like. If the brace element 21 is formed of a hollow tubular material, it may be necessary to insert a wood or plastic dowel 55 therein to prevent the tubular brace element from being crushed by the screw or rivet forces necessary to securely hold the plate 51 in place.

When secured to the base member bracing element 21 in this manner, each of the semi-circularly shaped ends 52 and 53 of the plate 51 extend above the brace element 21 to allow the attachment of the bracing bar (14 (or 15) of the upper portion 12 of the frame assembly 20 to be attached by means of a screw or rivet 56 which extends through the center point of a circle defined by each of the semi-circularly shaped ends 52 and 53 of the plate 51.

The brace member 14 can then rotate approximately 180 degrees about rivet 56 so as to be locatable at any position around the semi-circular ends 52 and 53 of the plate 51.

The exterior surface of the semi-circularly shaped ends 52 and 53 may contain a series of notches 57, and the brace bar 14 may have a pin 58 passing therethrough which extends beyond the exterior surface thereof in the direction of the semi-circularly shaped ends 52 and 53. The pin 58 may be formed such that it may be removed entirely from its position in the brace member 14 to allow for rotation thereof about rivet 56, and then may be replaced through the brace member 14 so as to be trapped in a set of notches 57, thus preventing further movement of the brace member 14 relative to the plate 51, which in turn prevents relative movement of the A-frame 12 and the lower portion 13' of the frame assembly 20.

Alternatively, the connection of the brace member 14 at the rivet 56 located at the center point of the semi-circularly shaped end pieces 52 and 53 may include an oval shaped opening 59 through the brace member 14 which extends in the longitudinal direction thereof. The oval shaped opening 59 allows the brace member 14 to be moved longitudinally a distance equal to the depth of the notches 57. In this alternative design, the pin 58 would be permanently fixed through the brace member 14 at a location where it would be trapped in the notches 57 when the brace member is pushed down into a first or locked position and would extend above the notches 57 allowing rotation of the brace member 14 when the brace member 14 is pulled into an extended or unlocked position. If desired, spring 60 may be attached to pin 58 and rivet 56. The spring 60 would hold the brace member 14 in its locked position until pulled to its extended or unlocked position by the user, after which it would return the brace member 14 back to its locked position.

Alternatively, if desired, the pin may be formed such that it may be pushed into the interior of the brace member 14 thereby avoiding entrapment in the notches 57, and the brace member 14 could then be rotated until the pin 58 is allowed to spring back into another notch location.

MODES OF OPERATION

In reference to the traction apparatus 10 embodiment of FIG. 4, the apparatus 10 is first placed on a level horizontal surface such as a floor, table, or bed and the user lays on the base member 19 such that the level of the base of the user's neck is centered along an imaginary line connecting the two attachment assemblies 40' and such that the length of the spine rests perpendicular to this imaginary line.

The headgear 16 can then be attached to the user's head. This procedure is described more specifically in applicant's co-pending patent application, Ser. No.

435272, filed 11/09/89. The upper portion 12 of the frame assembly 20 is then adjusted to lie approximately in the anticipated plane of the traction forces. Once the upper portion 12 of the frame assembly 20 is locked in position relative to the base member 19 of the lower portion 13' of the frame assembly 20, the handle 45 of the spring assembly 30' is securely gripped and pulled toward the user's head and the hook 44 associated with the handle 45 is attached to the headgear 16. Due to the nature of the constant force spring 39 used in the assembly 30' as shown in FIG. 4, the spring 39 must be pulled a distance of several inches in order to insure that it actually applies the preindicated constant force to the headgear 16. The user then remains in this position for the indicated therapy period. If it is desired to change the spring assembly 30' to a spring 39 having a different constant force, the entire spring assembly can be simply removed from the apex 11 of the frame assembly 20 by removing the attachment bolt 25' and replacing the entire spring assembly 30' with a new assembly.

In the case of the embodiment as shown in FIG. 1, the lower or body attachment portion 13 of the frame assembly 20 is positioned on the user's shoulders such that the attachment assemblies 40 are centered thereon and located at the base of the user's neck. The harness members 17 and 18 are then adjusted by loosening the knob 47 on the adjustment assemblies 40 and moving the harness members 17 and 18 as required to match the contours of the user's shoulders and upper torso. Further, if straps or other securing devices are included on the lower portion 13 of the frame assembly 20, they are attached around the user's torso in the indicated manner.

The upper portion 12 of the frame assembly is then adjusted to be located so that the anticipated line of force applied to the headgear 16 by the spring assembly 30 passes through a plane defined by the two attachment assemblies 40 and the apex 11 of the frame assembly 20 (the plane being represented as the line 64 in FIGS. 1 and 4). The knobs 47 on the attachment assemblies 40 are then retightened to lock the frame assembly 20 rigidly in this configuration.

The strap from the spring assembly is then connected to the headgear 16 and the traction force adjustment arm 33 is used to rotate the second bifurcated portion 28 of the spool 26. Rotation of the adjustment arm 33 rotates the torsion spring 36, which in turn attempts to rotate the opposite bifurcated portion 27 of the spool 26, which motion is countered by the attachment of the strap 31 to the headgear 16. The amount of rotation of the force adjustment arm 33, as can be obviously seen, controls the amount of traction force applied to the headgear 16.

The force adjustment arm 33 can be rotated to a point where it can easily be attached to a holding mechanism such as hook 61 extending from the brace member 15 of the upper portion 12 of the frame assembly 20. As will become obvious to one of ordinary skill in the art, adjustments may need to be made to the length of the strap 31, and/or to the location of a holding mechanism 61 for the adjustment arm 33, in order that the desired traction force can be achieved. For example, if it is desired that the predetermined traction force be applied at the time when the traction adjustment arm 33 is located directly parallel and adjacent to the bracing member 15 of the frame assembly 20, the length of the strap 31 extending between the spring assembly 30 and the headgear 16 must be adjusted so that the predetermined force is reached when the adjustment arm 33 arrives at its desired position adjacent the brace member 15. This can easily be accomplished through the use of an easily adjustable strap, such as a strap having loop and hook fasteners or a boat cleat type fastener.

As explained above in conjunction with the constant force spring assembly 30', the torsion spring assembly 30 can be removed from the frame assembly and replaced with another assembly having a different size of torsion spring 36 located therein.

ADVANTAGES OF THE PRESENT INVENTION OVER THE PRIOR ART

There are several advantages of the present invention over prior art systems. First, the traction apparatus 10 of the present invention can be completely self-contained, needing no exterior equipment or immobilization in order for it to perform its function.

Secondly, in the case of the frame assembly 20 as shown as part of the traction apparatus 10 of FIG. 1, the present invention while in use tends to encourage improvement of the user's posture by isolating and stretching the musculatures (trapezius) on the neck, and bringing the head up to its correct position over the spine. As can be seen, any degeneration of the user's posture tends to be counteracted by an increase in the traction force applied by the torsion spring assembly 30. Further, the present invention permits resistance in exercises, such as rear glide exercises and the like, which tend to strengthen the neck muscles to increase the ability of the neck to hold the head in a proper posture.

Third, the present invention provides a controlled angle of traction force whether the user is in the sitting or standing position.

Fourth, the attachment assemblies 40 and 40' allow adjustment of the upper and lower portions 12 and 13 (or 13') of the frame assembly 20, to a relative configuration which allows for the traction forces to be pulled substantially in the plane of the upper portion of the frame assembly (or at least in a plane defined by the apex 11 and the two attachment assemblies 40 or 40') in order to prevent or substantially eliminate moment loading of the frame. This feature allows the present invention to be built of less material and weight. Further, the attachment assemblies 40 or 40' allow the entire apparatus 10 to be easily folded into a compact portable unit.

A fifth advantage of the traction apparatus 10 of the present invention is that due to the fact that the apparatus as shown in FIG. 1 (employing the torsion spring assembly 30) is secured in place about the user's shoulders and torso (meaning, the user's shoulders and torso effectively counter the torsion force applied by the spring assembly), movement of the user's torso, arms and shoulders causes slight changes in the traction force applied when the torsion spring assembly 30 is used. These slight changes in tractional force, especially if they occur arrhythmically, can be a further aid to and increase the therapeutic effect of the traction. Alternatively, the embodiment of FIG. 1, if modified by changing the torsion spring assembly 30 with constant force spring assembly 30', causes the user to experience a constant traction force regardless of movements of the torso, arms or shoulders.

It is to be understood that the above-described arrangements are only illustrative of the application of the principles of the present invention. Numerous modifications and alternative arrangements may be devised by those skilled in the art without departing from the spirit and scope thereof. For example, the upper A-shaped portion 12 of the frame assembly 20 may be formed to lie entirely in a single plane as shown in FIG. 4, or may be formed to include an arch adjacent the apex 11 thereof. It is to be understood that either form of the A-frame 12 may be employed in any embodiment of the present invention.

Further, it is to be understood that the attachment assemblies 40 and 40' may be modified to include any wellknown type of adjustable attachment mechanism including a simple friction hinge mechanism, so long as it can be located at the base of the user's neck and attach the A-frame 12 to the lower portion 13 or 13'0 of the frame assembly 20 in a rigid yet adjustable manner.

Further, although not identified above, the constant force spring 39 and/or the torsion spring 36 may be sized to apply any traction force desired. It is contemplated, however, that the springs be sized to apply traction forces of approximately zero to 50 pounds, and more specifically to apply traction forces of approximately 10 to 35 pounds.

The apparatus 10 may be formed of any suitable materials such as metal, wood or plastic and of any suitable dimensions to accommodate the particular user. The particular materials and dimensions required being well within the understanding of one of ordinary skill in the art.

It also is felt to be within the understanding of one of ordinary skill in the art that the novel traction force generating devices, such as the spring assemblies 30 and 30' could be used in conjunction with other frame assemblies whether or not they incorporate the novel aspects of the frame assembly 20 of the present invention, or may be used independently of any frame assembly as by attaching it through a shackle or the like to an immovable object from which a user can attach the strap or hook member to the headgear 16 and use his body weight to counter the traction forces generated thereby.

We claim:

1. Traction apparatus comprising:
    frame assembly means having a first portion, a second portion, and an attachment means,
    said attachment means attaching said first portion to said second portion in an adjustable relationship,
    said first portion of said frame having two side members which extend above the user's head, and an apex which is located remotely from said attachment means and which includes means for attaching at least a portion of a traction force generating means thereto, said traction force generating means including head gear means and spring assembly means, said spring assembly means being attached to said apex and said head gear means being attachable to a user's head, said spring assembly means including a single attachment element which is attachable to said head gear means, and
    said second portion of said frame assembly including means for securing said second portion in fixed relationship relative to a user,
    whereby, when a user is correctly positioned relative to said second portion of said frame, said attachment means is located at the user's neck, above the user's shoulders and below the user's head, and allows adjustment of said first portion of said frame to any desired location relative to said second portion to orient the apex at the desired position above the user's head, and whereby, the connection of said attachment element between said spring assembly means and said head gear means functions to allow movement of the user's head relative to said frame for therapeutic purposes, without affecting the magnitude of the force applied to the head by the traction force generating means.

2. Traction apparatus according to claim 1 wherein said first portion of said frame assembly is adjustable at said hinge to allow traction forces applied to the user's head from said apex thereof to be directed substantially in the plane of said first portion.

3. Traction apparatus according to claim 1 wherein said securing means of said second portion includes means for securing said second portion about the shoulders and torso of a user, whereby, a traction apparatus can be used by the user while the user is in a standing or sitting position.

4. Traction apparatus according to claim 3 wherein said spring assembly means is entirely contained at the apex of said upper portion of said frame, whereby, the user is completely ambulatory while using the traction apparatus.

5. Traction apparatus according to claim 1 wherein said spring assembly includes a torsion spring.

6. Traction apparatus according to claim 1 wherein said spring assembly means includes a constant force spring.

7. Traction apparatus according to claim 1 wherein said second portion of said frame includes a flat base member, whereby, the flat base member may be located on a flat surface and the user may lie on said base member to secure said second portion of said frame relative to the user.

8. Traction apparatus according to claim 7 wherein said first portion of said frame can rotate relative to said second portion at said hinge means to a location wherein the apex of said first portion is adjacent to said base member.

9. Traction apparatus according to claim 1 wherein said spring assembly means includes a spring assembly comprising:
    a hollow bifurcated spool having a torsion spring located in the hollow interior thereof, said torsion spring having a first end and a second end, the first end of said torsion spring being attached to a first bifurcated portion of said spool and the second end of said torsion spring being attached to a second bifurcated portion of said spool, and
    a strap member attached to the exterior surface of the first bifurcated portion of said spool.

10. Traction apparatus according to claim 9 wherein said second bifurcated portion of said spool includes means for rotating said second bifurcated portion of said spool relative to said first bifurcated portion of said spool, whereby, movement of said rotating means causes an increase or decrease in the tension of said torsion spring.

* * * * *